United States Patent
Sheu et al.

(10) Patent No.: US 6,468,553 B1
(45) Date of Patent: Oct. 22, 2002

(54) FORMULA AND PREPARATION METHOD OF AN IMPROVED OINTMENT FOR TREATING BURNS AND SCALDS

(75) Inventors: Ce-Shing Sheu, Taichung (TW); Yi-Ching Wu, Taipei (TW); Jun-Hung Kuo, Panchiao (TW)

(73) Assignee: Pharmaceutical Industry Technology and Development Center, Taipei (TW)

( * ) Notice: Subject to any disclaimer, the term of this patent is extended or adjusted under 35 U.S.C. 154(b) by 0 days.

(21) Appl. No.: 09/631,813

(22) Filed: Aug. 3, 2000

(30) Foreign Application Priority Data

May 5, 2000 (TW) .......................... 89108597 A

(51) Int. Cl.⁷ .......................... A61K 9/06; A61K 35/78; A61K 7/48
(52) U.S. Cl. .................. 424/401; 424/78.06; 424/74; 424/7; 514/687; 514/887
(58) Field of Search ................... 514/682, 887; 424/401, 78.06, 74

(56) References Cited

U.S. PATENT DOCUMENTS 5,658,578 A * 8/1997 Ogawa et al. .............. 424/401
6,025,400 A * 2/2000 Lin .............................. 514/682

FOREIGN PATENT DOCUMENTS

CN   1152452 A   * 6/1997
WO   WO 9850055   * 11/1998

* cited by examiner

Primary Examiner—Jose' G. Dees
Assistant Examiner—Mina Haghighatian
(74) Attorney, Agent, or Firm—Fish & Richardson P.C.

(57) ABSTRACT

The invention discloses an extract containing puccoon and Chinese angelica, and a formula and preparation method of an ointment containing the extract. The extract is used for treating burns and scalds and is characterized by superior shelf-life. The puccoon and Chinese angelica are extracted with an organic solvent having a polarity of between 0.35 and 0.95, which are then filtrated, concentrated and mixed with a physiologically acceptable carrier or excipient.

8 Claims, 5 Drawing Sheets

FORMULA AND PREPARATION METHOD OF AN IMPROVED OINTMENT FOR TREATING BURNS AND SCALDS

BACKGROUND OF THE INVENTION

1. Field of the Invention

The present invention relates to an extract containing puccoon and Chinese angelica suitable for treating and/or ameliorating burns and scalds, and a formula and preparation method of an improved ointment containing the extract. More particularly, the present invention relates to an improved ointment, which is suitable for treating burns and scalds and which has an excellent shelf-life.

2. Description of the Related Arts

It is generally acknowledged that the Tzyy Yun Gau is one of the most effective externally applied medicines for treating burns and scalds. The Tzyy Yun Gau is described in ancient Chinese books and is primarily composed of sesame oil, butter, puccoon, Chinese angelica and yellow wax. In China and Japan, the ointment is widely used for treating cuts, abrasions, burns, frostbite, athlete's foot, helcosis, hemorrhoids, prolapse of the anus, acne (China Patent No. 1181264), etc. Traditional Tzyy Yun Gau is prepared by mixing puccoon, Chinese angelica, sesame oil and lard and soaking for 2 days, decocting with continuous heat and filtrating to remove residues, adding melted yellow wax, and stirring to form the ointment. Because the traditional Tzyy Yun Gau contains lipids such as sesame oil and lard, the product has a heavy oil odor and can suffer from putrefaction at an elevated temperature. In other words, the traditional Tzyy Yun Gau has a poor shelf-life.

Recent studies have shown that shikonin and derivatives thereof contained in puccoon (Arnebia euchroma) can reduce inflammation, prevent infection, relieve pain and promote granulation tissue proliferation (U.S. Pat. No. 4,282,250), whereas the components in Chinese angelica (*Angelica sinensis* Radix) can prevent thrombus formation, ameliorate blood circulation, and also reduce inflammation and promote skin wound healing in animal trials. Therefore, the components of puccoon and Chinese angelica in the traditional Tzyy Yun Gau play an important role in the effectiveness of the ointment in treating burns.

However, shikonin and derivatives thereof contained in puccoon are very sensitive to acids, bases, light, temperature, etc., and are non-stable. Further, the component, ligustilide, contained in Chinese angelica is also non-stable. All these factors will affect the shelf-life of the Tzyy Yun Gau. Thus, there is a need to improve the shelf-life of the Tzyy Yun Gau to maintain the effectiveness of the active ingredients after long term storage.

Burns and scalds are common accidents in life. A first degree burn injury invades the epithelia and results in a wound that has slight inflammation and pain, but can heal completely. A superficial secondary degree burn injury results in slight scars. However, deep secondary and third degree burn injuries invade dermal and subcutaneous tissues, and most of the follicles and sebaceous glands are destroyed. Obvious scars appear after healing and usually affect function and outward appearance. The patients suffer very much and may need skin grafts. There are many medicines and methods for treating burns and scalds. Generally, the therapy uses drugs such as antiphlogistics, antiseptics or analgesics, to mitigate inflammation, prevent infection or relieve pain or discomfort of patients. A biological dressing (such as pigskin) or non-biological dressing (such as Biobrane®) is also employed to facilitate the wound healing. However, most of the current drugs are not useful in the regeneration of the skin tissue. They only provide and maintain a suitable environment for the wound to heal itself.

SUMMARY OF THE INVENTION

It is therefore a primary object of the present invention to provide an extract for treating burns or scalds, in which puccoon and Chinese angelica are extracted with an organic solvent having a polarity of between 0.35 and 0.95 (assuming that the polarity of water equals to 1), and are then filtrated and concentrated to obtain the extract.

Another aspect of the present invention is to provide a method for preparing the effective extract for treating burns or scalds, comprising the steps of: extracting Chinese angelica and puccoon with an organic solvent having a polarity of between 0.35 and 0.95 at a temperature below 40° C. for 4~48 hours; filtrating and concentrating the extract at a temperature below 40° C.; wherein the extraction of Chinese angelica and puccoon can be performed separately or at the same time.

Yet another aspect of the present invention is to provide a formula of an oily ointment used for treating burns or scalds, which is characterized by superior shelf-life, comprising an effective amount of extract of Chinese angelica and puccoon, and one or more physiologically acceptable carrier(s) or excipient(s).

Still another aspect of the present invention is to provide a method of preparing an oily ointment used for treating burns or scalds, comprising mixing an effective amount of extract of Chinese angelica and puccoon with a lipid; mixing one or more physiologically acceptable carrier(s) or excipient(s) with the mixture described above at 50° C.~100° C.; and stirring the mixture until the mixture contains no bubbles, and slowly cooling the mixture to room temperature. Another method of preparing an oily ointment used for treating burns or scalds comprises melting one or more physiologically acceptable carrier(s) or excipient(s) at 50° C.~100° C.; mixing an effective amount of extract of Chinese angelica and puccoon with the mixture described above; and stirring the mixture until the mixture contains no bubbles, and slowly cooling the mixture to room temperature.

The present invention uses puccoon and Chinese angelica as primary starting materials, and uses other lipids in lieu of sesame oil and lard to improve the preparing process and increase the stability of the obtained ointment. In addition, pharmacological experiments have shown the treatment effect of the Tzyy Yun Gau prepared by the present invention is better than that of the traditional Tzyy Yun Gau. Furthermore, in the extract of the present invention in which puccoon and Chinese angelica are extracted with organic solvents, the amount of shikonin is much higher than that in the traditional Tzyy Yun Gau.

BRIEF DESCRIPTION OF THE FIGURE

The present invention will be more fully understood and further advantages will become apparent when reference is made to the following description of the invention and the accompanying drawings in which.

DETAILED DESCRIPTION OF THE INVENTION

Figure 1:
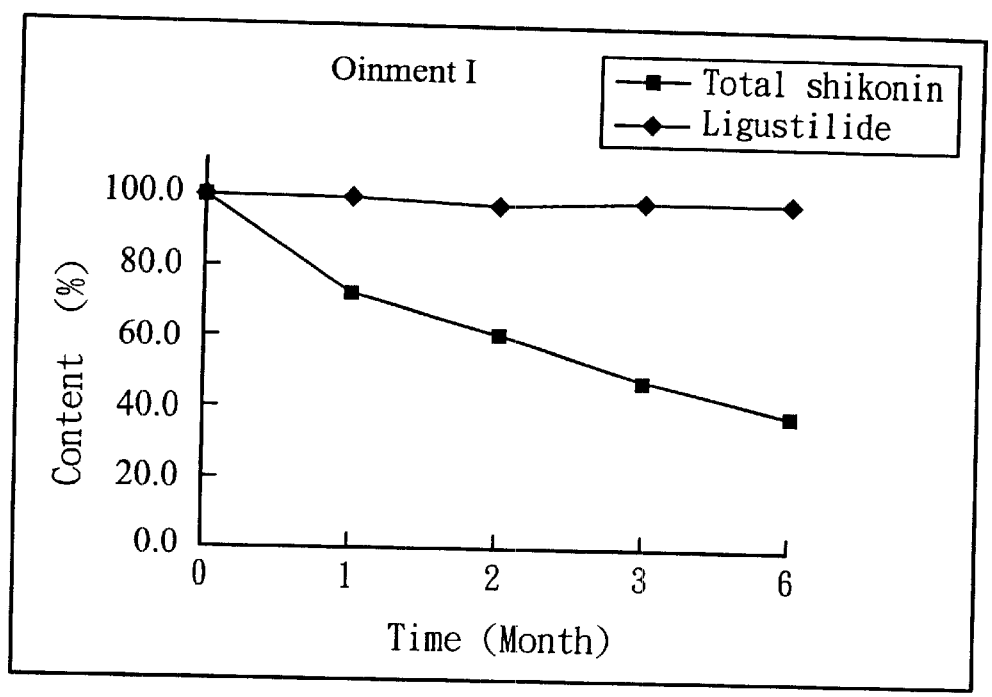
FIG. 1 is a diagram showing stability analysis of the traditional Tzyy Yun Gau (ointment I)

In accordance with the present invention, puccoon and Chinese angelica are extracted with an organic solvent having a polarity of between 0.35 and 0.95 (assuming that the polarity of water equals to 1), and are then filtrated and concentrated to obtain an effective extract. The "puccoon" used herein refers to *Arnebia euchroma* or *Lithospermum erythrorhizon*, whereas the "Chinese angelical" refers to *Angelica sinensis*. It is well known to one of ordinary skill in the art that organic solvents having a polarity of between 0.35 and 0.95 include, but are not limited to, $C_1$~$C_4$ lower alcohol (such as, preferably, methanol, ethanol or isopropanol) or ethyl acetate. Puccoon and Chinese angelica can be extracted separately with the organic solvents described above, followed by mixing the two extracts, or extracted together. The extraction is performed at a lower temperature, preferably at a temperature below 40° C., for a period ranging from 4 to 48 hours to form an extract of puccoon and Chinese angelica. Afterwards, the extract is filtrated to remove residues and then concentrated at a temperature below 40° C. to obtain an effective extract, wherein the concentration method can be performed in any manner known to one skilled in this art.

The present invention provides a formula of an oily ointment comprising the extract of puccoon and Chinese angelica described above and one or more physiologically acceptable carrier(s) or excipient(s), which is used for treating burns or scalds and characterized by superior shelf-life. Due to the excellent shelf-life, the Tzyy Yun Gau of the present invention can avoid putrefaction during the period of storage. The key point is using the lipids whose acid value is less than 2 mg-KOH/g, and the physiologically acceptable carrier or excipient which can stabilize the formula of the present invention, thereby preparing an oily ointment having efficacy of treating burns and scalds and excellent shelf-life.

The physiologically acceptable carrier or excipient used in the formula of the present invention can comprise $C_{14}$~$C_{22}$ fatty acid, wax, lipid, glycerol, $C_{14}$~$C_{22}$ alcohol or synthetic lipid. As described above, the lipids used herein should have an acid value less than 2 mg-KOH/g. Examples of suitable lipids include mineral oil, silicon oil, petrolatum or vegetable oil, wherein the examples of vegetable oil comprise castor oil, olive oil, soybean oil, palm oil or sesame oil. Examples of suitable $C_{14}$~$C_{22}$ fatty acids include stearic acid, oleic acid, myristic acid or behenic acid; example of $C_{14}$~$C_{22}$ alcohol include cetyl alcohol, stearyl alcohol, cholesterol, palmityl alcohol or behenyl alcohol; and examples of synthetic lipid include, for example, glyceryl mono-oleate, hegrogenated castor oil, isopropyl myristate or isopropyl palmitate.

The present invention also provides a method of preparing an oily ointment used for treating burns or scalds comprising the steps of: mixing an extract of Chinese angelica and puccoon with a lipid; adding one or more physiologically acceptable carrier(s) or excipient(s) to the mixture described above at 50° C.~100° C.; and then stirring the mixture until the mixture contains no bubbles, and slowly cooling the mixture to room temperature. Another preparation method comprises melting one or more physiologically acceptable carrier(s) or excipient(s) at 50° C.~100° C. to form a paste-like mixture; mixing an extract of Chinese angelica and puccoon with the paste-like mixture described above; and then stirring the paste-like mixture until the mixture contains no bubbles, and slowly cooling the mixture to room temperature.

According to the method of the present invention, the extract of Chinese angelica and puccoon is mixed with a suitable lipid at first to form an encapsulated structure, thereby protecting the active ingredient (particularly shikonin) in the extract from the degradation during the subsequent heating process. It is understood that melting suitable carrier or excipient first and then slowly adding the extract of Chinese angelica and puccoon to the melted mixture described above under the suitable conditions and temperature is also an acceptable method avoiding the degradation of the active ingredient. The method of stirring the paste-like mixture to remove bubbles is well-known in the art and not limited to a particular method. Preferably, the stirring is performed in vacuum or under an inert atmosphere.

Without intending to limit it in any manner, the present invention will be further illustrated by the following examples.

EXAMPLE

Example 1

Preparation Method of Traditional Tzyy Yun Gau

1. Extraction of Medicinal Materials 81.25 g of sesame oil, 12 g of puccoon and 6 g of Chinese angelica (all available on the Taiwanese market) were mixed in a stirring machine (Heidolph RZR 2051) equipped with a heater (CORNING PC-620) set at 1300C with 200~300 rpm and heated to 130° C. The mixture was continuously heated at this temperature for 30 minutes. The decoction was filtrated with three layers of gauze while it was still hot to obtain the first filtrate. The first filtrate was re-filtrated with a filter (Advantec No. 1, 185 mm) by an air pump to obtain the filtrate I.

2. Preparation of Tzyy Yun Gau 30 g of yellow wax was added to the filtrate I with stirring and heating to 70° C.~75° C. The heating was stopped when the yellow wax melted completely, and then the mixture was continuously stirred until the temperature decreased to 35° C.~45° C. The ointment I (Traditional Tzyy Yun Gau) was obtained when the mixture solidified completely.

Example 2

Preparation Method of Tzyy Yun Gau Improved by Refined Sesame Oil

All the parameters were the same as in EXAMPLE 1, except that 81.25 g of sesame oil was changed to refined sesame oil (ACROS ORGANICS, NJ, USA). The filtrate II and ointment II (Tzyy Yun Gau improved by refined sesame oil) were subsequently obtained.

Example 3

Preparation Method of Tzyy Yun Gau Improved by Soybean Oil

All the parameters were the same as in EXAMPLE 1, except that 81.25 g of sesame oil was changed to soybean oil (commercially available). The filtrate III and ointment III (Tzyy Yun Gau improved by soybean oil) were subsequently obtained.

Example 4

1. Extraction of Medicinal Materials 54 ml of isopropanol was added to a container containing 12 g of puccoon and 6 g of Chinese angelica. The mixture was soaked for 48 hours, followed by filtrating with a filter (Advantec No. 1, 185 mm). The extract was then concentrated under reduced pressure at 20° C.~25° C. to obtain about 3.4 g of the extract IV.

2. Preparation of Tzyy Yun Gau 14.5 g of mineral oil, 2.9 g of stearyl alcohol, 7.7 g of white wax, 2.9 of cholesterol and 68.6 g of petrolatum were added to the extract IV (14.3 g), and heated at 75° C. for 30 minutes. The heating was stopped when the components melted completely and became transparent, and then the mixture was continuously stirred (55 rpm) until the temperature decreased to 45° C. The mixture was then stirred in vacuum for 3~5 minutes to remove bubbles and the ointment IV was obtained.

Example 5

1. Extraction of Medicinal Materials

The extraction method was the same as in EXAMPLE 4.

2. Preparation of Tzyy Yun Gau 22.89 g of stearyl alcohol, 4.64 g of stearic acid, 4.64 g of polyethylene glycol 6000 (PEG-6000) and 64.35 g of propylene glycol were heated to 75° C. The heating was stopped when the components melted completely and became transparent, and then the mixture was continuously stirred (55 rpm) until the temperature decreased to 55° C.~60° C. The mixture was added to the extract IV (3.4 g), and stirred until the temperature decreased to 35° C.~40° C., followed by stirring in vacuum for 3~5 minutes to remove bubbles and the ointment V was obtained.

Example 6

Stability Analysis of the Index Component in Product

The storage conditions of the stability analysis were described as follows. The temperature was set at 4° C., 30° C. and 40° C., respectively, and the relative humidity (RH) was 75%. The products were sampled on the 0, $1^{st}$, $2^{nd}$, $3^{rd}$, and $6^{th}$ month for the examination of color, odor and properties. In addition, the amounts of the active ingredients of ligustilide and total shikonin in each sample were analyzed by HPLC, wherein the total shikonin was calculated with the combination of shikonin, acetylshikonin and ββ-dimethylacryl-shikonin. The results are shown in Table 1 and FIGS. 1–5.

TABLE 1

Records of appearance at 40° C. and 75% RH.

| Ointment Type | property | 0 month | $1^{st}$ month | $2^{nd}$ month | $3^{rd}$ month | $6^{th}$ month |
|---|---|---|---|---|---|---|
| I | Crimson ointment with odors of sesame oil and angelica | Identical color | Deeper color | Deeper color | Deeper color; thinner odor of sesame oil | Deeper color; thinner odor of sesame oil |
| II | Claret ointment with odors of sesame oil and angelica | Identical color | Identical color | Identical color | Identical color | Identical color |
| III | Claret ointment with odors of soybean oil and angelica | Identical color | Identical color | Identical color | Identical color | Identical color |
| IV | Deep-red ointment with odors of slight isopropanol and angelica | Identical color | Identical color | Identical color | Identical color | Identical color |
| V | pink ointment with odors of slight isopropanol and angelica | Identical color | Deeper color of blue-purple | Deeper color of blue-purple | Deeper color of blue-purple | Deeper color of blue-purple and fractionated |

Figure 2:
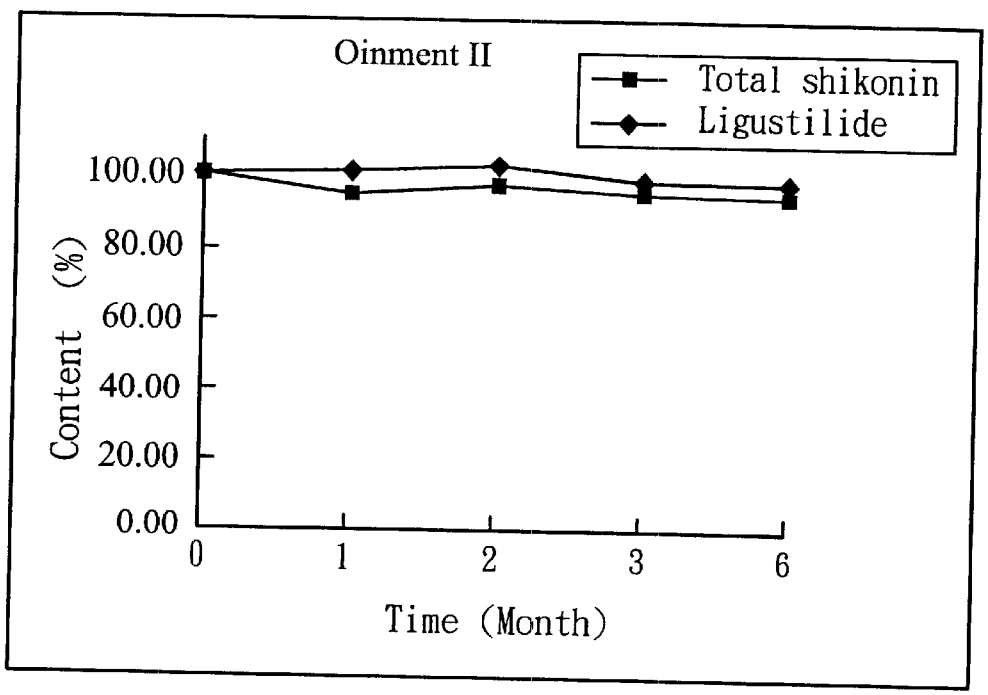
FIG. 2 is a diagram showing stability analysis of the Tzyy Yun Gau improved by refined sesame oil (ointment II)
Figure 3:
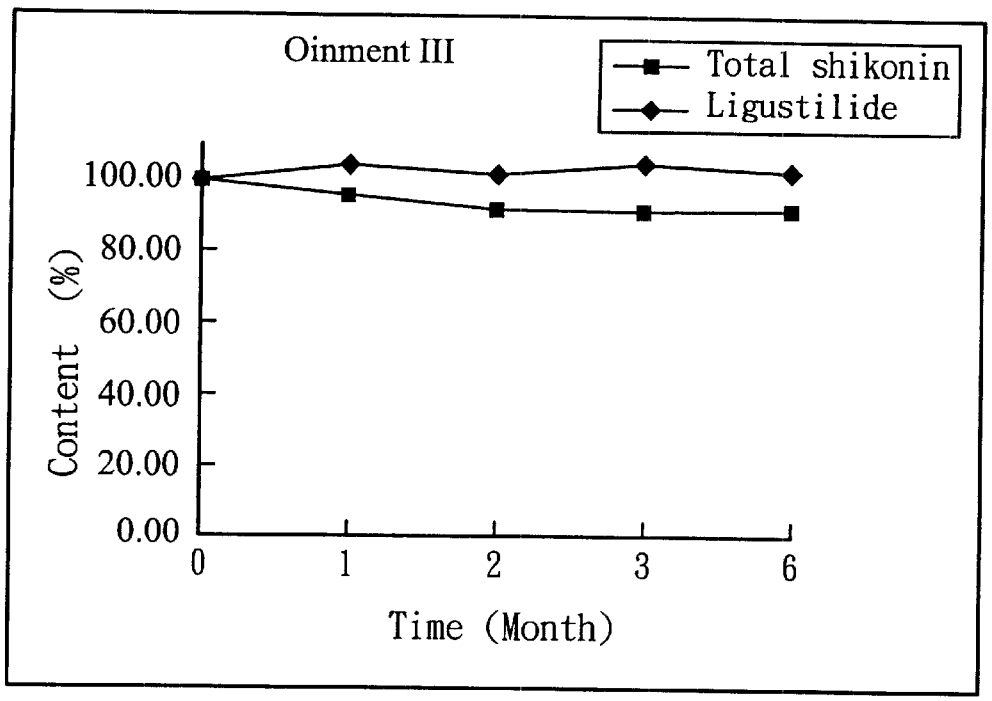
FIG. 3 is a diagram showing stability analysis of the Tzyy Yun Gau improved by soybean oil (ointment III)
Figure 4:
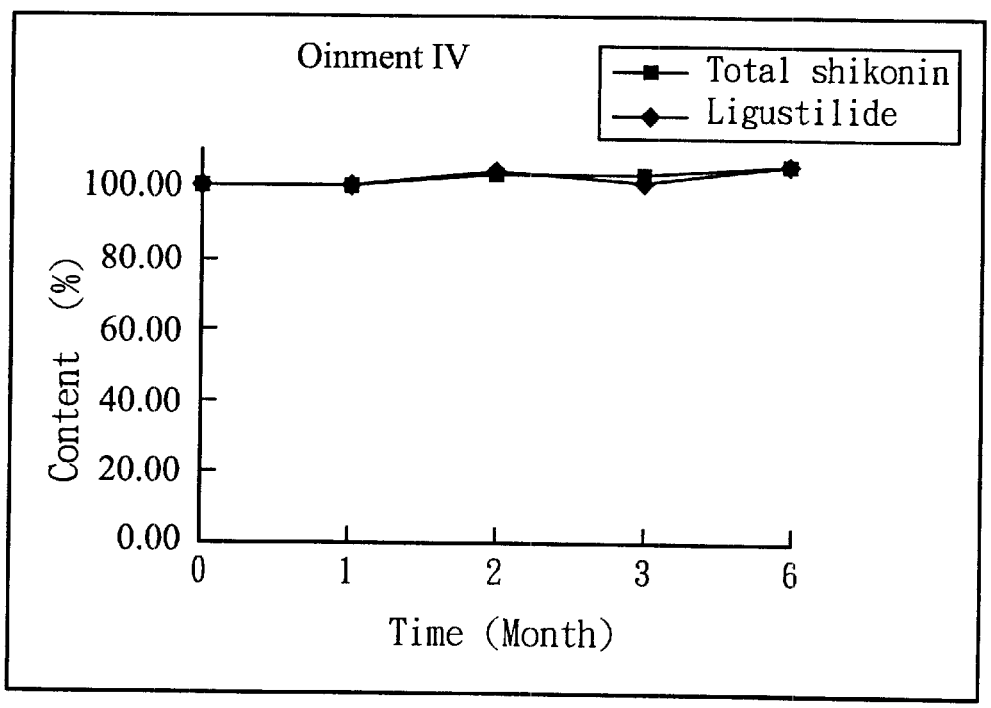
FIG. 4 is a diagram showing stability analysis of the improved Tzyy Yun Gau of a first embodiment of the present invention (ointment IV)
Figure 5:
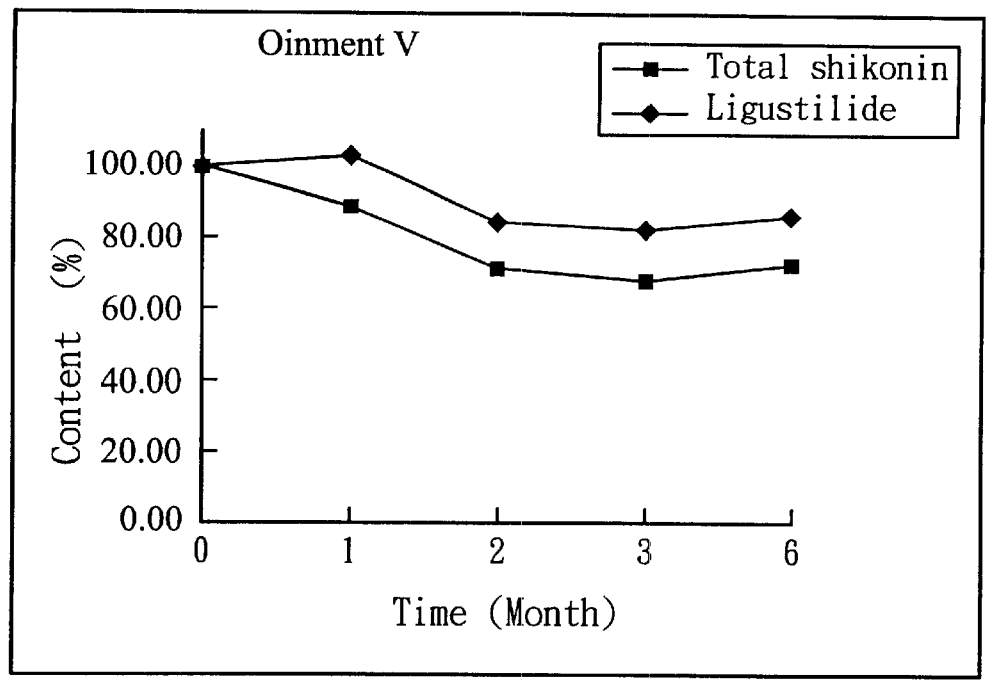
FIG. 5 is a diagram showing stability analysis of the improved Tzyy Yun Gau of a second embodiment of the present invention (ointment V)

Result:

The quantitative analysis during 6 months shows the amount of ligustilide in various ointments varies insignificantly, while the amount of total shikonin varies significantly. Referring to FIG. 1, with the increase of time, the amount of total shikonin rapidly decreases, reflecting the non-stability of the traditional Tzyy Yun Gau (ointment I). In contrast, the amount of total shikonin in the improved Tzyy Yun Gau keeps at a steady level after 6 months storage even under the conditions of such a high temperature as 40° C. Referring to FIGS. 2–4, ointment IV is the most stable, and the next is Tzyy Yun Gau improved by refined sesame oil or soybean oil, wherein the difference of total shikonin amount in the improved Tzyy Yun Gau is less than that in the traditional Tzyy Yun Gau after 6 months. It is clearly shown that Tzyy Yun Gau improved by the method of the present invention can elevate the stability. Ointment IV has the best shelf-life among the 5 ointments.

Example 7

In Vitro Releasing Test

Figure 6:
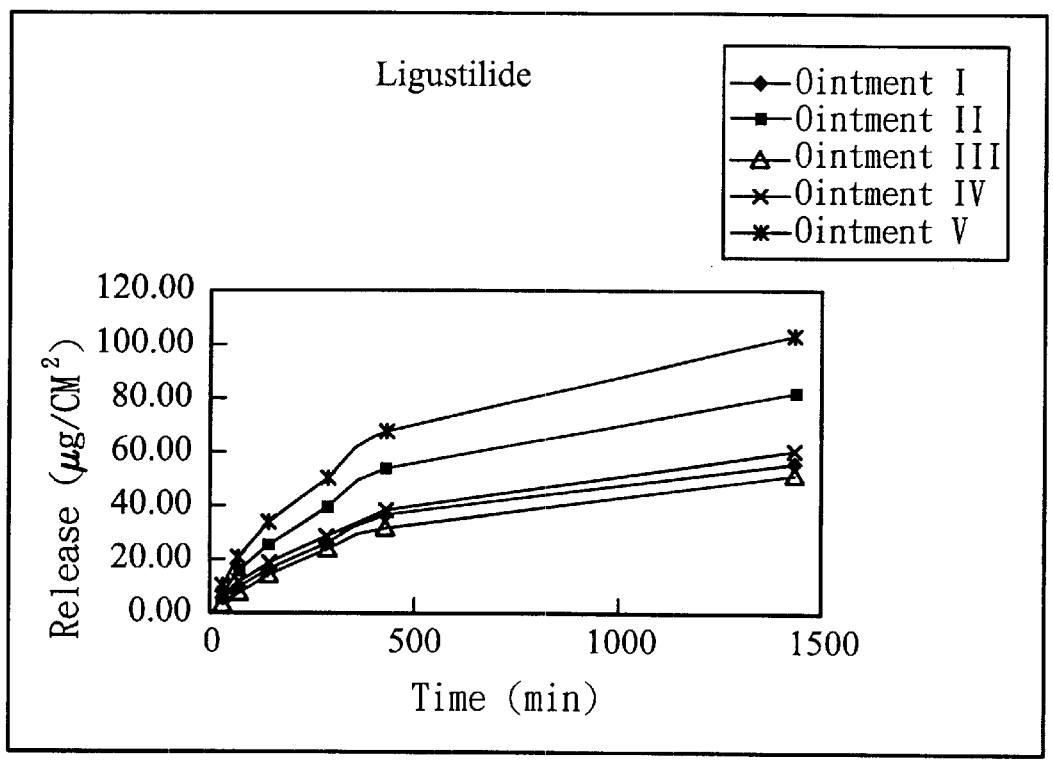
FIG. 6 is a diagram showing the release of ligustilide in various ointments in an in vitro releasing test.
Figure 7:
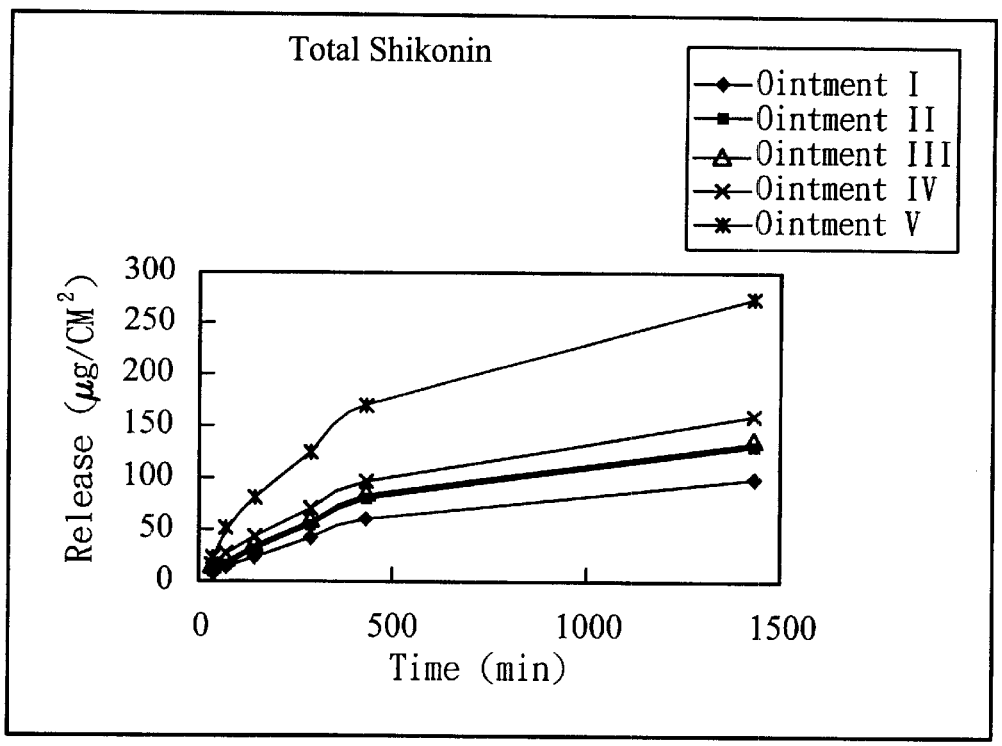
FIG. 7 is a diagram showing the release of total shikonin in various ointments in an in vitro releasing test.

Each ointment was filled into the upper panel of a Franz diffusion cell (9-mm diameter, 6-ml volume, PMC DATAPLATE). A stirrer was inserted and 6 ml of degassed receptor phase (60:40, phosphate saline buffer: isopropanol, wherein the phosphate saline buffer was prepared by 66.7 mM KH2PO4 and 66.7 mM $K_2HPO_4$, pH 5.0) pre-heated to 32° C. was poured into lower panel avoiding bubble formation. A 0.45-μm filter (Hydrophobic Durapore Membrane, Millipore) was placed between upper and lower panels and clipped. The Franz diffusion cell was placed in a 32° C. thermostatic chamber with stirring. Each ointment was sampled 1 ml at 36, 72, 144, 288, 432 and 1440 minutes, followed by filtrating with a 0.45-$\mu$m filter. After each sampling, 1 ml of receptor phase pre-heated to 32° C. was added to the cell to maintain constant volume. The amount of ligustilide and total shikonin was analyzed by HPLC, respectively. The results are shown in Tables 2–3 and FIGS. 6–7.

TABLE 2

Release of ligustilide in an in vitro releasing test

| Time (min) | Ointment I ($\mu$g/cm$^2$) | Ointment II ($\mu$g/cm$^2$) | Ointment III ($\mu$g/cm$^2$) | Ointment IV ($\mu$g/cm$^2$) | Ointment V ($\mu$g/cm$^2$) |
|---|---|---|---|---|---|
| 36 | 4.06 | 6.82 | 4.31 | 5.25 | 9.88 |
| 72 | 9.04 | 14.56 | 9.40 | 11.02 | 20.22 |
| 144 | 16.06 | 25.16 | 15.94 | 17.88 | 33.33 |
| 288 | 26.12 | 39.09 | 24.42 | 27.53 | 50.60 |
| 432 | 36.16 | 53.54 | 33.59 | 37.87 | 67.57 |
| 1440 | 56.10 | 81.56 | 51.11 | 60.51 | 102.95 |

TABLE 3

Release of total shikonin in an in vitro releasing test

| Time (min) | Ointment I ($\mu$g/cm$^2$) | Ointment II ($\mu$g/cm$^2$) | Ointment III ($\mu$g/cm$^2$) | Ointment IV ($\mu$g/cm$^2$) | Ointment V ($\mu$g/cm$^2$) |
|---|---|---|---|---|---|
| 36 | 5.48 | 7.63 | 7.80 | 11.84 | 22.57 |
| 72 | 13.08 | 17.11 | 18.73 | 25.97 | 47.99 |
| 144 | 23.30 | 32.30 | 35.49 | 43.90 | 80.62 |
| 288 | 41.27 | 55.61 | 58.48 | 69.81 | 125.67 |
| 432 | 59.29 | 80.80 | 84.61 | 98.00 | 170.97 |
| 1440 | 96.26 | 131.06 | 133.82 | 157.29 | 274.09 |

Result:

The results of the in vitro releasing test reveal that the permeabilities of ligustilide and total shikonin are different. The ligustilide analysis shows the permeabilities of ointments II and V are better than that of the traditional Tzyy Yun Gau, whereas the total shikonin analysis shows the permeabilities of all improved ointments are better than that of the traditional Tzyy Yun Gau, wherein the ointments IV and V are the best.

Example 8

Pharmacological Assessment of the Activity of Tzyy Yun Gau

1. Model of Pharmacological Assessment

[a]. Animals: SD rats, weighting 400~450 g, were anesthetized with 45 mg/kg Pentothal (i.p.). The dorsal hair was shaved and then a 120° C. heat source was used to contact the exposed region for 4 seconds, producing 6 spots of 3×3 cm$^2$ of deep secondary degree burn injury.

[b]. Experimental animals: The wounds of the burned rat were treated with the improved Tzyy Yun Gau (ointment IV) of the present invention twice per day for a period of 14 days.

[c]. Negative control: The wounds of the burned rat were covered with swabs only.

[d]. Positive control: The wounds of the burn rat were treated with a conventional drug used clinically for burns, silver sulphadiazine cream (Mari, USA), twice per day for 14 days.

2. Items of Assessment

[a]. Rate of wound healing: The wound area was measured on the $2^{nd}$, $4^{th}$, $9^{th}$ and $14^{th}$ day after burn injury and the healing percentage was calculated.

[b]. Blood flux: The blood flux was measured on the $2^{nd}$, $4^{th}$, $9^{th}$ and $14^{th}$ day after burn injury by laser Doppler flowmetry (Moor LD17636, Moor Instruments Ltd., UK) as an indication of the recovery of the wound.

[c]. Biopsy: The wounds were sampled 1×1 cm$^2$ on the $2^{nd}$, $4^{th}$, $9^{th}$ and $14^{th}$ day after burn injury and stained with hematoxylin to observe: (i) displacement rate of epithelia regeneration; (ii) arrangement of collagen; and (iii) concentration of inflammatory cells. The level of the physiological phenomenon was classified into 4 classes, which were bad, acceptable, good and excellent, and scored 2, 4, 6 and 8, respectively. The results were judged by the sum of the scores of the 3 items described above, and shown in Tables 4–5 and FIGS. 8–9.

TABLE 4

Rate of the wound healing

| Group | $9^{th}$ day (%) | $14^{th}$ day (%) |
|---|---|---|
| Negative control | 15.8 | 83.9 |
| Positive control | 16.8 | 30.7 |
| Ointment I | 4.3 | 47.8 |
| Ointment II | 17.1 | 66.8 |
| Ointment III | 25.0 | 100 |
| Ointment IV | 74.8 | 100 |
| Ointment V | 6.7 | 50.0 |

TABLE 5

Scores of biopsy on the $14^{th}$ day after burn injury

| Group | Arrangement of collagen | displacement rate of epithelia regeneration | Conc. of inflammatory cells | score |
|---|---|---|---|---|
| Negative control | 5 | 5 | 7 | 17 |
| Positive control | 4 | 5 | 6 | 15 |
| Ointment I | 6 | 6 | 7 | 19 |
| Ointment II | 5 | 6 | 7 | 18 |
| Ointment III | 6 | 7 | 6 | 19 |
| Ointment IV | 7 | 8 | 7 | 22 |
| Ointment V | 7 | 7 | 6 | 20 |

Figure 8:
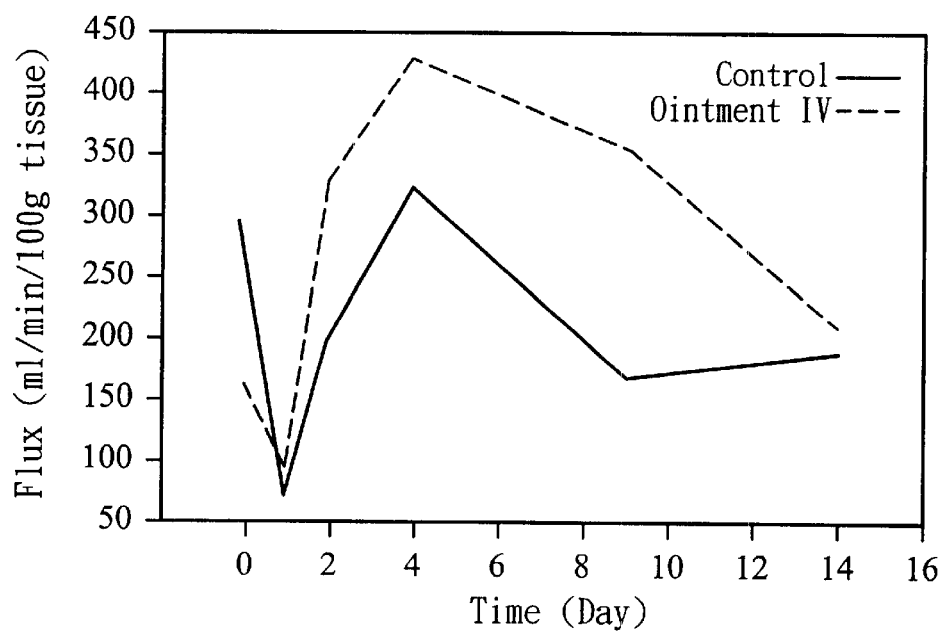
FIG. 8 is a diagram showing effects of the improved Tzyy Yun Gau of the present invention on the wound blood flux measured by laser Doppler flowmetry.
Figure 9A:
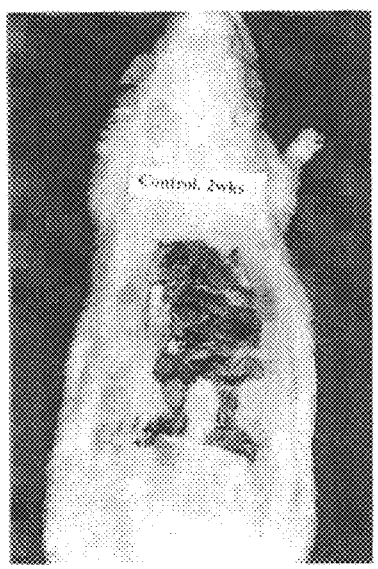
FIGS. 9(A, B, & C) show the pharmacological assessment of the activity of the Tzyy Yun Gau on rats, wherein (A) shows a negative control without any application; (B) shows a positive control, on which a conventional drug, silver sulphadiazine cream, for treating burns is applied; and (C) shows an experiment group, on which the improved Tzyy Yun Gau of the present invention (ointment IV) is applied.
Figure 9B:
Figure 9C:

Referring to Table 4, it is shown the healing rate of the negative control is only 15.8% whereas that of the ointment III and IV is 25% and 74.8%, respectively, on the $9^{th}$ day; and reaches to 100% on the $14^{th}$ day. The blood flux at the wound region measured by laser Doppler flowmetry reveals the blood flux of the ointment IV is better recovered than that of the traditional Tzyy Yun Gau (the line left shifting; FIG. 8). In addition, the result of the biopsy shows the ointment IV has an excellent healing effect. Moreover, referring to FIGS. 9(A)–(C), it is shown that the recovery effect of the wound treated with the improved Tzyy Yun Gau (ointment IV) of the present invention is much better than that treated with silver sulphadiazine cream in the positive control.

From various results shown above, it is demonstrated that the effect and shelf-life of the improved Tzyy Yun Gau (particularly ointment IV) of the present invention are much better than those of the traditional Tzyy Yun Gau, indicating the methods and formulas of the present invention indeed elevate the stability and activity of the product.

While the invention has been particularly shown and described with the reference to the preferred embodiment thereof, it will be understood by those skilled in the art that various changes in form and details may be made without departing from the spirit and scope of the invention.

What is claimed is:

1. A method of preparing an oily ointment used for treating burns or scalds, comprising the steps of:
   (a) mixing an effective amount of extract comprising puccoon and Chinese angelica, with a lipid having an acid value less than 2 mg-KOH/g to obtain a mixture;
   (b) mixing a physiologically acceptable carrier or excipient with said mixture from step (a) at 50° C.~100° C.; and
   (c) stirring said mixture from step (b) until that said mixture contains no bubbles, and slowly cooling said mixture to room temperature.

2. A method of preparing an oily ointment used for treating burns and scalds, comprising the steps of:
   (a) melting a physiologically acceptable carrier or excipient selected from a lipid having an acid value less than 2 mg-KOH/g at 50° C.–100° C. to form a paste-like mixture;
   (b) mixing an effective amount of extract comprising puccoon and Chinese angelica with said paste-like mixture; and
   (c) stirring said mixture from step (b) until said mixture contains no bubbles, and slowly cooling said mixture to room temperature.

3. The method according to claim 1, wherein the stirring step is performed in vacuum.

4. The method according to claim 1, wherein said lipid comprises mineral oil, silicon oil, petrolatum or vegetable oil.

5. The method according to claim 4, wherein said vegetable oil comprises castor oil, olive oil, soybean oil, palm oil or sesame oil.

6. The method according to claim 2, wherein the stirring step is performed in vacuum.

7. The method according to claim 2, wherein said lipid is mineral oil, silicon oil, petrolatum or vegetable oil.

8. The method according to claim 7, wherein said vegetable oil is castor oil, olive oil, soybean oil, palm oil or sesame oil.

* * * * *